(12) United States Patent
Tsuboi et al.

(10) Patent No.: US 8,460,918 B2
(45) Date of Patent: Jun. 11, 2013

(54) LACTIC ACID BACTERIA HAVING ACTION OF LOWERING BLOOD URIC ACID LEVEL

(75) Inventors: Hiroshi Tsuboi, Kanagawa (JP); Noriko Kaneko, Kanagawa (JP); Akina Satou, Kanagawa (JP); Yoshinobu Tsuchiya, Kanagawa (JP)

(73) Assignee: Meiji Co., Ltd., Kanagawa (JP)

( * ) Notice: Subject to any disclaimer, the term of this patent is extended or adjusted under 35 U.S.C. 154(b) by 202 days.

(21) Appl. No.: 12/745,007

(22) PCT Filed: Nov. 29, 2007

(86) PCT No.: PCT/JP2007/073108
§ 371 (c)(1),
(2), (4) Date: Sep. 14, 2010

(87) PCT Pub. No.: WO2009/069219
PCT Pub. Date: Jun. 4, 2009

(65) Prior Publication Data
US 2011/0014168 A1    Jan. 20, 2011

(51) Int. Cl.
*C12N 1/20*    (2006.01)
(52) U.S. Cl.
USPC .................................... 435/252.9; 424/93.45
(58) Field of Classification Search
None
See application file for complete search history.

(56) References Cited

U.S. PATENT DOCUMENTS

| | | | | |
|---|---|---|---|---|
| 6,340,585 B1 * | 1/2002 | Elli et al. | | 435/252.9 |
| 2010/0316618 A1 | 12/2010 | Tsuboi et al. | | |

FOREIGN PATENT DOCUMENTS

| | | |
|---|---|---|
| CN | 1812801 A | 8/2006 |
| EP | 1649863 A1 | 4/2006 |
| EP | 2221359 | 8/2010 |
| JP | 2008/005834 A | 1/2008 |
| TW | 200507862 | 3/2005 |
| WO | WO2004/112809 A1 | 12/2004 |
| WO | WO 2006/067940 | 6/2006 |

OTHER PUBLICATIONS

Kwak C. et al., Prevention of nephrolithiasis by Lactobacillus in stone-forming rats: a preliminary study, Urol. Res., (2006), vol. 34, pp. 265-270.*
Koll-Klais P. et al., Oral lactobacilli in chronic periodontitis and periodontal health: species composition and antimicrobial activity, Oral Microbiology Immunology, 2005, vol. 20, pp. 354-361.*
Kumemura M. et al, Composition for Lowering Serum Uric Acid Level, WO 2004/112809A1, English translation done on Nov. 28, 2005, total pp. 1-42.*
Prevent-term defined by Merriam-Webster online dictionary—at the web: http://www.merriam-webster.com/dictionary/prevent; pp. 1-2.*
Shimizu T. et al., Effects of Lactobacillus gasseri OLL 2716 (LG21) on Helicobacter pylori infection in children, Journal of Antimicrobial Chemotherapy, 2002, vol. 50, provided only pertinent pp. 617-618.*
Aslim, B. et al, Some Probiotic Properties of Vaginal Lactobacilli Isolated from Healthy Women, Jpn. J. Infect. Dis, 59 (4):249-253, 2006.
Extended European Search Report, EP07832808.5, dated Oct. 4, 2011.
Friedman, Eli A. et al, Gut-Based Uremia Therapy: Simultaneous Removal of Urea, Creatinine, and Uric Acid, J. American Society of Nephrology, Williams and Wilkins, Baltimore, MD, V12(Suppl):71A-72A, Jan. 1, 2001.
John A. E. Farrow et al, Lactobacillus oris sp. nov. from the Human Oral Cavity, Int. J. of Systemic Bacteriology 38:1[116-118], Jan. 1988.
International Search Report, PCT/JP2007/073108, mailed Dec. 25, 2007.
J. Ogawa et al., The proceedings of Annual meeting of Japanese Society for Bioscience, Biotechnology, and Agrochemistry, 2005, p. 244, V. 2005.
T. Ikenaga, et al., The proceedings of the 58th Annual Meeting of Japanese Society of Nutrition and Food Science, 2004, p. 318, V. 58.
T. Ikenaga, et al., The proceedings of Annual meeting of Japanese Society for Bioscience, Biotechnology, and Agrochemistry, 2004, p. 197, V. 2004.
Office Action for U.S. Appl. No. 13/544,756 mailed Dec. 12, 2012, 15 pages.
Supplemental Office Action for U.S. Appl. No. 13/544,756 mailed Dec. 27, 2012, 15 pages.
Koll-Klais, P. et al., Oral lactobacilli in chronic periodontitis and periodontal health: species composition and antimicrobial activity, Oral Microbiology Immunology, 20[354-361], 2005.
U.S. Appl. No. 13/544,756, filed Jul. 9, 2012, Tsuboi et al.
Office Action for U.S. Appl. No. 12/745,006, mailed Jun. 28, 2012, 13 pages.
Azcarate-Peril, M. et al., "Analysis of the genome sequence of lactobacillus gasseri ATCC 33323 reveals the molecular basis of an autochthonous intestinal organism," Applied and Environmental Microbiology, 74(15):4610-4625 (2008).
Extended European Search Report for European Application No. EP08854151.1, dated Oct. 4, 2011, 7 pages.

(Continued)

*Primary Examiner* — Jon P Weber
*Assistant Examiner* — Satyendra Singh
(74) *Attorney, Agent, or Firm* — Cooley LLP

(57) ABSTRACT

Various types of lactic acid bacteria were cultured in the presence of a purine, the amount of the purine consumed and the amount of purine degradation products produced were measured, and several lactic acid bacteria showing remarkable purine-decomposing ability were selected. Lactic acid bacteria that were assessed to have high purine-decomposing ability according to the above-mentioned selection were orally administered to rats reared on purine-containing feed, the general status and serum uric acid level of the rats were measured, and the effect of lactic acid bacteria administration on serum uric acid levels was examined. As a result, lactic acid bacteria that significantly suppress the increase of serum uric acid levels, *Lactobacillus gasseri* OLL2959 and *Lactobacillus oris* OLL2779, were found.

9 Claims, 5 Drawing Sheets

OTHER PUBLICATIONS

International Search Report for International Application No. PCT/JP2008/071559, mailed Dec. 22, 2008, 2 pages.
International Preliminary Report on Patentability for International Application No. PCT/JP2008/071559, mailed Aug. 19, 2010, 7 pages.
Lauer, E. et al., "Lactobacillus gasseri sp. nov., a new species of the subgenus thermobacterium," Zbl. Bakt., I. Abt. Orig. C 1, 75-78 (1980).
Ogawa, J. et al., "The proceedings of annual meeting of Japanese Society for Bioscience, " Biotechnology and Agrochemistry, 2004:197 (2004).

* cited by examiner

LACTIC ACID BACTERIA HAVING ACTION OF LOWERING BLOOD URIC ACID LEVEL

CROSS REFERENCE TO RELATED APPLICATIONS

This application is a National Stage Entry Application of PCT Application No. PCT/JP2007/073108, filed Nov. 29, 2007. The entire disclosures of the prior applications are incorporated herein by reference.

TECHNICAL FIELD

The present invention relates to lactic acid bacteria that have an effect of lowering the blood uric acid level and methods for using them, and also relates to foods or pharmaceuticals that comprise lactic acid bacteria for preventing and/or treating hyperuricemia.

BACKGROUND ART

Hyperuricemia is a condition of reduced uric acid excretion or excessive uric acid production due to environmental (lifestyle) or genetic factors, and leads to excess uric acid in the blood. Although hyperuricemia may lack subjective symptoms, it causes serious complications such as gout, renal dysfunction, urolithiasis, and arteriosclerosis. Acute arthritis with severe pain appears as a major symptom in gout, a representative complication of hyperuricemia. Gout was once called "the regal disease" and had been a "luxury disease" of those in the ranks that frequently consumed a lot of meat, fish, alcohol, and such; however, recently, it has been increasing yearly due to changes in the diet. The current population of gout patients in Japan is 300,000 to 400,000 people, and the population of hyperuricemia patients is estimated to be 6,000,000; thus, prevention and treatment of hyperuricemia is drawing increasing attention.

Prevention and treatment of hyperuricemia is carried out by controlling the uric acid level in blood through diet therapy, exercise therapy, pharmaceuticals, and combinations thereof. In particular, limiting caloric intake is one of the most frequently selected methods for preventing and treating hyperuricemia, but maintaining strict calorie restriction is not always easy. As a method for improving such circumstances, methods for lowering the serum uric acid level by orally ingesting microorganisms such as lactic acid bacteria and yeast that decompose purines (for example as pharmaceuticals or dietary products), and decomposing purines ingested from meals in the intestine to decrease their absorption into the body have been suggested (Patent Document 1 and Non-patent Document 1). Lactic acid bacteria have been traditionally used as foods and pharmaceuticals, and since they are highly safe to the human body, consumption of lactic acid bacteria can be an effective method for preventing/treating hyperuricemia with little concern for side effects. Furthermore, as described above, the first choice of methods for preventing and treating hyperuricemia is diet therapy, and by ingesting lactic acid bacteria that allow control of uric acid levels as food, it may become a novel and very realistic, effective method for preventing and/or treating hyperuricemia. Although the lactic acid bacteria reported in the above-mentioned documents, *Lactobacillus fermentum* and *Lactobacillus pentosus*, are capable of decomposing purines, they have gas-producing ability and are not necessarily suitable bacterial species in terms of application as dietary products and pharmaceuticals.

[Patent Document 1] WO 2004/112809
[Non-patent Document 1] Homepage of the Japan Society for Bioscience, Biotechnology, and Agrochemistry (JSBBA), Annual Meeting of JSBBA Lecture and Presentation Database (which can be found on the World Wide Web at jsbba.bioweb.ne.jp/jsbba_db/index.html) "JSBBA 2004.03.30 general lecture, Ikenaga, T., Kumemura, M. et al.: Effects of lactic acid bacteria on the blood uric acid levels of dietary hyperuricemia model rats."

DISCLOSURE OF THE INVENTION

Problems to be Solved by the Invention

The present invention was achieved in view of the above circumstances. An objective of the present invention is to provide lactic acid bacteria that are capable of preventing and/or treating hyperuricemia, which are suitable for use in dietary products or pharmaceuticals, and at the same time to provide compositions that use the above-mentioned lactic acid bacteria for preventing and/or treating hyperuricemia.

Means for Solving the Problems

The present inventors persistently made dedicated efforts to solve the above-mentioned problems. First, various lactic acid bacteria were cultured in the presence of inosine and guanosine, and the amount of the above-mentioned nucleosides consumed and the amount of degradation products (hypoxanthine and guanine) produced were determined. Then, several lactic acid bacteria with remarkable nucleoside-decomposing ability were selected. Lactic acid bacteria assessed to have high nucleoside-decomposing ability according to the above-mentioned selection were orally administered to rats reared on purine-containing feed, the general status and the serum uric acid level of the rats were measured, and the effect of lactic acid bacteria administration on the serum uric acid level was examined. As a result, lactic acid bacteria which significantly suppress the increase of serum uric acid level were found: *Lactobacillus oris* OLL2779 and *Lactobacillus gasseri* OLL2959. Furthermore, the present inventors prepared yogurt using the above-mentioned lactic acid bacteria to confirm that the above-mentioned lactic acid bacteria are suitable for processing foods including yogurt. Since the lactic acid bacteria of the present invention suppress the increase of serum uric acid levels, they can be used effectively as pharmaceuticals for preventing or treating hyperuricemia or gout. Furthermore, since it has been confirmed by experiments that the lactic acid bacteria of the present invention have the effect of suppressing the increase of serum uric acid levels through oral administration and are suitable for actual food processing, their applicability is remarkably high because they can be used as food. Thus, the present invention relates to lactic acid bacteria capable of preventing and/or treating hyperuricemia and uses thereof. Specifically, the present invention provides the following:

[1] a lactic acid bacterium of the genus *Lactobacillus*, wherein the bacterium has purine-decomposing ability but not gas-producing ability;

[2] the lactic acid bacterium of [1] described above, wherein the bacterium is *Lactobacillus gasseri*;

[3] a lactic acid bacterium *Lactobacillus oris*, wherein the bacterium has purine-decomposing ability;

[4] the lactic acid bacterium of the genus *Lactobacillus* of [2] described above, wherein the bacterium is *Lactobacillus gasseri* OLL2959 (Accession No.: NITE BP-224);

[5] the lactic acid bacterium of the genus *Lactobacillus* of [3] described above, wherein the bacterium is *Lactobacillus oris* OLL2779 (Accession No.: NITE BP-223);

[6] a dietary product for suppressing an increase in blood uric acid level, which comprises the lactic acid bacterium of any one of [1] to [5] described above, a substance containing said lactic acid bacterium, and/or a processed material thereof;

[7] a pharmaceutical for suppressing an increase in blood uric acid level, which comprises the lactic acid bacterium of any one of [1] to [5] described above, a substance containing said lactic acid bacterium, and/or a processed material thereof;

[8] a pharmaceutical for preventing and/or treating hyperuricemia, which comprises the lactic acid bacterium of any one of [1] to [5] described above, a substance containing said lactic acid bacterium, and/or a processed material thereof;

[9] a dietary product for preventing and/or treating hyperuricemia, which comprises the lactic acid bacterium of any one of [1] to [5] described above, a substance containing said lactic acid bacterium, and/or a processed material thereof;

[10] a method for suppressing the level of purine ingested from food, wherein the method comprises administering the lactic acid bacterium of any one of [1] to [5] described above, a substance containing said lactic acid bacterium, and/or a processed material thereof;

[11] a method for suppressing an increase in blood uric acid level, wherein the method comprises administering the lactic acid bacterium of any one of [1] to [5] described above, a substance containing said lactic acid bacterium, and/or a processed material thereof;

[12] a method for producing a dietary product with reduced purine level, wherein the method comprises the step of contacting a raw material or intermediate product of the dietary product with the lactic acid bacterium of any one of [1] to [5] described above, a substance containing said lactic acid bacterium, and/or a processed material thereof;

[13] a method for treating and/or preventing any one or more diseases or symptoms from the group consisting of hyperuricemia, gout, renal dysfunction, urolithiasis, and artheriosclerosis, wherein the method comprises administering the lactic acid bacterium of any one of [1] to [5] describe above, a substance containing said lactic acid bacterium, and/or a processed material thereof; and

[14] use of the lactic acid bacterium of any one of [1] to [5] described above, a substance containing said lactic acid bacterium, and/or a processed material thereof in the manufacture of a dietary product and/or pharmaceutical for suppressing an increase in blood uric acid level in a subject of administration.

BEST MODE FOR CARRYING OUT THE INVENTION

Figure 1:
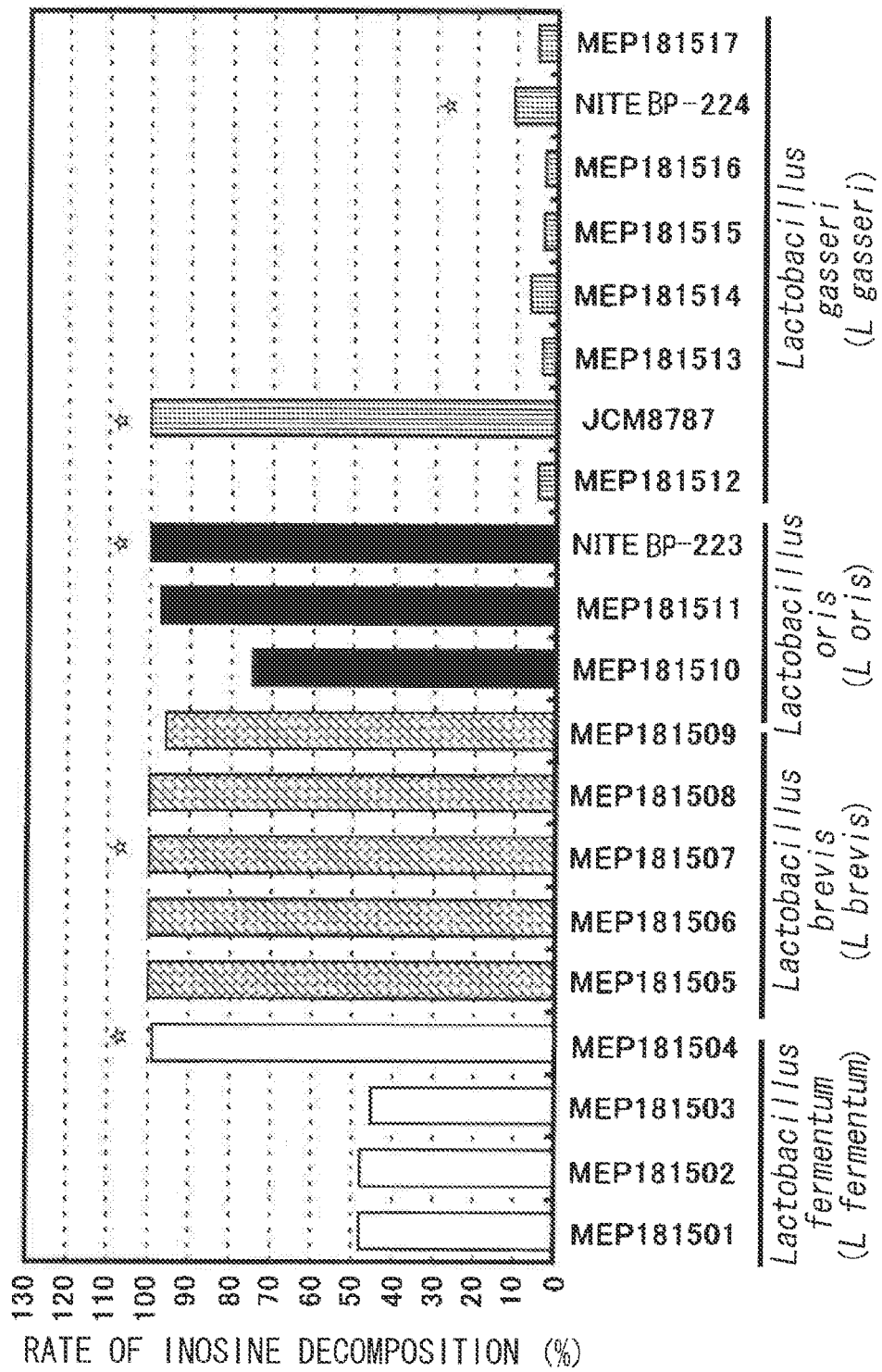
FIG. 1 shows the purine-decomposing ability of each of the lactic acid bacteria when they were cultured in the presence of a purine (inosine). Bacterial strains confirmed to have high purine-degradation rate (indicated with stars) were used as subjects of animal model experiment.

The present invention relates to lactic acid bacteria of the genus *Lactobacillus* that have purine-decomposing ability and not gas-producing ability. The present invention is based on the present inventors' initial discovery of lactic acid bacteria of the genus *Lactobacillus* that have purine-decomposing ability and not gas-producing ability (hereinafter also referred to as "lactic acid bacteria of the genus *Lactobacillus* of the present invention").

The genus *Lactobacillus* is one of the representative genera of lactic acid bacteria, and includes 80 or more species. Examples of species included in *Lactobacillus* are *Lactobacillus delbrueckii* subsp. *burgalicus*, *Lactobacillus delbrueckii* subsp. *lactis*, *Lactobacillus paracasei* subsp. *paracasei*, *Lactobacillus helveticus*, *Lactobacillus helveticus* subsp. *jugurti*, *Lactobacillus acidophilus*, *Lactobacillus crispatus*, *Lactobacillus amylovorus*, *Lactobacillus gallinarum*, *Lactobacillus gasseri*, *Lactobacillus oris*, *Lactobacillus casei* subsp. *rhamnosus*, *Lactobacillus johnsonii*, *Lactobacillus fermentum*, and *Lactobacillus brevis*. The lactic acid bacteria of the genus *Lactobacillus* of the present invention may be any species as long as they are lactic acid bacteria of the genus *Lactobacillus* that have purine-decomposing ability and not gas-producing ability, and they are preferably *Lactobacillus gasseri*.

Purines are components that constitute nucleic acids, and they are supplied to the living body through de novo purine synthesis, salvage pathway, nucleoproteins in the diet, and such, and unnecessary purines are metabolized in the liver and then excreted. Uric acid is the final metabolite of purines in humans, higher primates, birds, reptiles, and such.

Herein, purines are compounds that comprise a purine skeleton. Representative examples of purines include purine nucleotides (adenylic acid, deoxyadenylic acid, guanylic acid, and deoxyguanylic acid), purine nucleosides (adenosine, deoxyadenosine, guanosine, and deoxyguanosine), purine bases (adenine and guanine), and oligonucleotides and polynucleotides comprising purine bases. Purine bases constitute, besides nucleic acids, a wide variety of biological components such as ATP, GTP, cAMP, cGMP, coenzyme A, FAD, and NAD. All of such biological components are also included in the purines herein as long as they comprise a purine skeleton.

Purines in a living body are metabolized to uric acid. The metabolic pathways from purines to uric acid are well known. 5'-Nucleotidase converts AMP to adenosine which is converted to hypoxanthine via inosine. 5'-Nucleotidase converts GMP to guanosine which then becomes guanine. Hypoxanthine and guanine are metabolized by xanthine oxidase and guanine deaminase, respectively, both giving xanthine, and xanthine oxidase further converts xanthine to uric acid.

Purine-decomposing ability in the present invention refers to the ability to decompose at least one purine, regardless of whether the degradation product comprises a purine skeleton. Thus, the ability to decompose a certain purine into a compound that does not comprise a purine skeleton, and the ability to decompose a certain purine to form a different purine (a compound comprising a purine skeleton) are both included in the purine-decomposing ability of the present invention.

Lactic acid bacteria of the genus *Lactobacillus* of the present invention can be separated by known methods. For example, they can be isolated by culturing bacteria obtained from the feces of mammals such as humans, separating *Lactobacillus* based on the form, physiological characteristics, and such of the cultured bacteria; detecting the presence or absence of purine-decomposing ability and gas-producing ability; and then selecting *Lactobacillus* which has purine-decomposing ability but not gas-producing ability. Detection of purine-decomposing ability and gas-producing ability can be performed by known methods, and as an example, they can be performed by the methods in the Examples.

Media that are generally suitable for culturing lactic acid bacilli may be used for culturing the lactic acid bacteria of the genus *Lactobacillus* of the present invention, and media comprising carbon sources such as glucose, lactose, galactose, fructose, trehalose, sucrose, mannose, and cellobiose; nitrogen sources such as meat extracts, peptone, yeast extracts, casein, and whey proteins; and inorganic nutrients such as magnesium sulfate, iron sulfate, and manganese sulfate can be used. One preferable example includes Lactobacilli MRS Broth (Difco). The culture conditions are not particularly restricted, as long as the growth of intestinal lactobacilli is possible. Preferable conditions include, for example, pH5.0 to pH8.0, and temperature of 20° C. to 45° C., and more preferable conditions are anaerobic, pH5.0 to pH7.0, and temperature of 30° C. to 40° C.

As described later, the present inventors orally administered the lactic acid bacteria of the genus *Lactobacillus* of the present invention to model animals, and confirmed that these lactic acid bacteria have an effect of suppressing the increase of blood uric acid levels. Therefore, lactic acid bacteria of the genus *Lactobacillus* of the present invention can be used to suppress the increase in blood uric acid levels or prevent and/or treat hyperuricemia. Furthermore, it may be possible to manufacture foods that contain a reduced amount of purines using the purine-decomposing ability of the lactic acid bacteria of the genus *Lactobacillus* of the present invention.

Specific examples of "lactic acid bacteria of the genus *Lactobacillus* having purine-decomposing ability but not gas-producing ability" in the present invention include *Lactobacillus gasseri* OLL2959 specified by Accession No.: NITE BP-224. The present inventors examined the presence or absence of purine-decomposing ability and gas-producing ability for a large number of lactic acid bacteria, and specifically found that the lactic acid bacteria of the genus *Lactobacillus* named *Lactobacillus gasseri* OLL2959 has purine-decomposing ability but not gas-producing ability. Furthermore, they determined through in vivo experiments that *Lactobacillus gasseri* OLL2959 significantly suppresses the increase in blood uric acid level. The present inventors deposited the above-mentioned bacterial strain with the Patent Microorganisms Depositary (NPMD) of the National Institute of Technology and Evaluation. Contents specifying the deposit are described below.

(A) Depositary institution: Patent Microorganisms Depositary (NPMD) of the National Institute of Technology and Evaluation (Location: 2-5-8, Kazusakamatari, Kisarazu-city, Chiba, 292-0818, Japan)

(B) Original date of deposition: Mar. 31, 2006
Date of transfer from domestic deposit to deposit under the Budapest Treaty: Nov. 21, 2007

(C) Accession No.:
*Lactobacillus Gasseri* Strain OLL2959 (Accession No.: NITE BP-224)

Furthermore, the present invention relates to *Lactobacillus oris* (lactic acid bacteria) which has purine-decomposing ability. The present invention is based on the present inventors' initial discovery of lactic acid bacteria *Lactobacillus oris* which have purine-decomposing ability (hereinafter, also referred to as "lactic acid bacteria *Lactobacillus oris* of the present invention").

*Lactobacillus oris* (lactic acid bacteria) of the present invention can be separated and cultured by a method similar to the above-described method for separation and culture of lactic acid bacteria of the genus *Lactobacillus* of the present invention. Furthermore, lactic acid bacteria *Lactobacillus oris* of the present invention can also be used for suppressing the increase in blood uric acid levels, or prevention and/or treatment of hyperuricemia.

Specific examples of "*Lactobacillus oris* (lactic acid bacteria) with purine-decomposing ability" of the present invention include *Lactobacillus oris* OLL2779 specified by Accession No.: NITE BP-223. From a large number of lactic acid bacteria, the present inventors found *Lactobacillus oris* OLL2779 as a lactic acid bacterium having purine-decomposing ability, and discovered through in vivo experiments that *Lactobacillus oris* OLL2779 significantly suppresses the increase in blood uric acid levels. The present inventors deposited the above-mentioned bacterial strain with the Patent Microorganisms Depositary (NPMD) of the National Institute of Technology and Evaluation. Contents specifying the deposit are described below.

(A) Depositary institution: Patent Microorganisms Depositary (NPMD) of the National Institute of Technology and Evaluation (Location: 2-5-8, Kazusakamatari, Kisarazu-city, Chiba, 292-0818, Japan)

(B) Original date of deposition: Mar. 31, 2006
Date of transfer from domestic deposit to deposit under the Budapest Treaty: Nov. 21, 2007

(C) Accession No.:
*Lactobacillus Oris* Strain OLL2779 (Accession No.: NITE BP-223)

Lactic acid bacteria of the genus *Lactobacillus* of the present invention and lactic acid bacteria *Lactobacillus oris* of the present invention can be used to manufacture dietary products or pharmaceuticals for suppressing the increase in blood uric acid levels, and dietary products or pharmaceuticals for preventing and/or treating hyperuricemia.

Dietary products prepared using the lactic acid bacteria of the genus *Lactobacillus* of the present invention and lactic acid bacteria *Lactobacillus oris* of the present invention are not limited in terms of their category or type and may be functional food, specified health food, health food, nursing care food, or may be dairy products such as confectionary, lactic acid bacteria beverage, cheese, or yogurt, flavoring agents, or such. The form of the dietary product is also not limited, and may take the form of any dietary product that may be commonly distributed such as a solid, liquid, fluid diet, jelly, tablets, granules, or capsules. The above-mentioned dietary products can be manufactured through methods that are ordinary to those skilled in the art. In producing the above-mentioned dietary products, carbohydrates, proteins, lipids, dietary fibers, vitamins, biologically essential trace metals (manganese sulfate, zinc sulfate, magnesium chloride, potassium carbonate, etc.), flavors, or other compositions may be added, as long as they do not interfere with the growth of lactic acid bacteria.

The lactic acid bacteria of the genus *Lactobacillus* of the present invention and lactic acid bacteria *Lactobacillus oris* of the present invention, material containing these lactic acid bacteria and/or processed material thereof (for example, culture, concentrate, paste material, spray-dried material, freeze-dried material, vacuum-dried material, drum-dried material, fluid material, dilution material, and homogenate) can be processed into common dietary products comprising dairy products/fermented milk as described above, and used as starters for producing dairy products/fermented milk such as yogurt and cheese. When they are used as starters, other microorganisms may be admixed as long as they do not interfere with the manufacturing of dairy products or the inhabitation/proliferation of the lactic acid bacteria of the genus *Lactobacillus* of the present invention and lactic acid bacteria *Lactobacillus oris* of the present invention. For example, they may be admixed with *Lactobacillus delbruekii* subsp. *bulgaricus, Streptococcus thermophilus*, or *Lactobacillus acidophilus* which are major bacterial species of lactic acid bacteria in yogurt, and additionally, they may be admixed with bacterial species generally used for yogurt or cheese and made into starters. Dairy products and fermented milk can be manufactured using the above-mentioned starters by ordinary methods. For example, plain yogurt can be manufactured by admixing the above-mentioned starter with milk or dairy products that have been subjected to heating, mixing, homogenization, sterilization treatment, and cooling, followed by fermentation and cooling.

The lactic acid bacteria of the genus *Lactobacillus* of the present invention and lactic acid bacteria *Lactobacillus oris* of the present invention can be admixed with physiologically acceptable carriers, excipients, diluting agents, or such, and administered orally or parenterally as pharmaceutical compositions; however, the preferred method of administration is oral administration. Formulations for oral administration can be prepared as various well-known dosage forms, and such examples include granules, powders, tablets, pills, capsules, liquids, syrups, emulsions, suspensions, and troches. Furthermore, by preparing an enteric-coated formulation by methods well-known to those skilled in the art, the lactic acid bacteria of the genus *Lactobacillus* of the present invention can be transported efficiently to the intestine without being affected by gastric acid.

Pharmaceuticals and dietary products manufactured using the lactic acid bacteria of the genus *Lactobacillus* of the present invention and lactic acid bacteria *Lactobacillus oris* of the present invention can be expected to display an effect of suppressing the increase in blood uric acid levels or an effect of preventing and/or treating hyperuricemia through the actions of these bacteria in the dietary products.

Furthermore, by using the purine-decomposing ability of the lactic acid bacteria of the genus *Lactobacillus* of the present invention and lactic acid bacteria *Lactobacillus oris* of the present invention, dietary products with reduced purine levels can also be manufactured. Methods of the present invention for manufacturing dietary products with reduced purine levels comprise the step of contacting the lactic acid bacteria of the genus *Lactobacillus* of the present invention and lactic acid bacteria *Lactobacillus oris* of the present invention with a raw material or intermediate product of the dietary product. This step efficiently reduces the amount of purine contained in the raw materials or intermediate products. The above-mentioned step is preferably carried out under conditions in which the lactic acid bacteria of the genus *Lactobacillus* of the present invention and lactic acid bacteria *Lactobacillus oris* of the present invention are viable. In addition to the above-mentioned step, the manufacturing method of the present invention may comprise common steps for manufacturing dietary products of interest such as a crushing step, admixing step, drying step, sterilization step, and packing step. Dietary products manufactured by the methods of the present invention are not limited in terms of their category or type and may be, for example, functional food, specified health food, health food, nursing care food, or common food, for example, food categorized as tasty food; however, they are particularly useful as a daily dietary product or supplementary dietary product for patients with a disease or symptom that requires limiting purine intake, or the high-risk group for the above-mentioned disease or symptoms. The methods of the present invention enable people who need to limit their purine intake or people who want to control their purine intake to consume foods normally high in purine level and enjoy their nutrients or taste.

All prior art references cited herein are incorporated by reference into this description.

EXAMPLES

Herein below, the present invention will be specifically described with reference to the Examples, but it is not to be construed as being limited thereto. In the Examples, the bacterial strains indicated as JCM in the bacterial strain name are standard strains obtained from the Japan Collection of Microorganisms RIKEN BioResource Center, the bacterial strains indicated as ATCC in the bacterial strain name are standard strains obtained from the American Type Culture Collection, and the bacterial strains indicated as MEP in the bacterial strain name are bacterial strains held by Meiji Dairies Corporation.

Example 1

In Vitro Experiment Method on the Uric Acid-Reducing Effect of Lactic Acid Bacteria The following method was used to examine the presence or absence of purine-decomposing ability in each type of lactic acid bacteria.

Using a Difco Lactobacilli MRS Broth (manufactured by BD) medium, each type of lactic acid bacteria (bacterial cells) was placed in a sealed container with an oxygen adsorbing agent "AnaeroPack" (manufactured by Mitsubishi Gas Co.) and anaerobically cultured overnight at a temperature of 37° C. The bacterial suspension solution obtained after culturing was subjected to centrifugal separation at a rotation frequency of 3000 rpm for 10 minutes at a temperature of 4° C. to precipitate and collect (harvest) the bacterial cells.

A $1 \times 10^9$ CFU/mL bacterial cell suspension solution was prepared from these bacterial cells using a 0.1 M sodium phosphate buffer.

After preparing the various types of bacterial cell suspension solutions, inosine and guanosine were each added at 1.25 mM to every bacterial cell suspension solution. These bacterial cell suspension solutions were placed in a 37° C. constant temperature bath, and then shake cultured at a horizontal rotation frequency of 140 rpm for 30 minutes or two hours.

The consumption level of nucleosides and the production level of bases (hypoxanthine and guanine), which are degradation products of nucleosides, in the shake cultured bacterial cell suspension solutions (reaction solutions) were measured on HPLC using 5-bromouracil as the internal standard. 200 µL of the reaction solution was added to 780 µL of mobile phase A, and 20 µL of 5-bromouracil (1.6 mg/mL) was added as the internal standard and mixed. This mixed solution was filtered with a filter (pore size 0.45 µm), and then 50 µL of the filtered solution was injected into HPLC. The specific operational conditions of the HPLC are as follows.

HPLC: Waters alliance 2690

Column: CAPCELL PAK $C_{18}$ SG120, particle diameter 5 µm, column size 4.6×250 mm (Shiseido)

Mobile phase: A: 25 mM $KH_2PO_4$ (0.1% methanol)

B: 25 mM $KH_2PO_4$ (0.1% methanol)/methanol (75:25)

gradient A/B (min): 100/0 (0)-100/0 (10)-20/80 (20)-20/80 (25)-100/0 (26)-100/0 (40)

Detector: photodiode array (Waters 996) detection wavelength of 254 nm

Flow rate: 1 mL/min

Column temperature: room temperature

Figure 2:
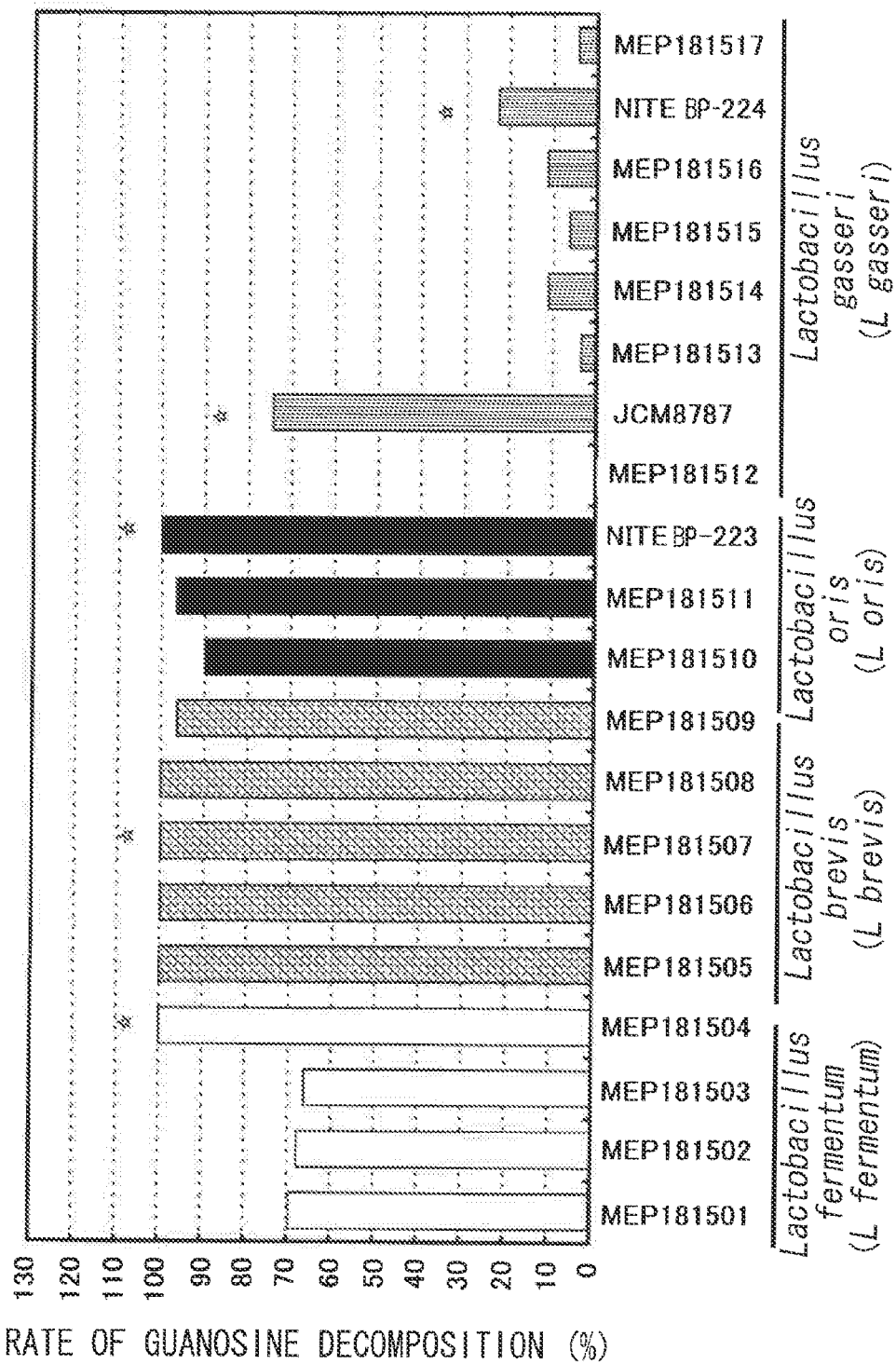
FIG. 2 shows the purine-decomposing ability of each of the lactic acid bacteria when they were cultured in the presence of a purine (guanosine). Bacterial strains confirmed to have high purine-degradation rate (indicated with stars) were used as subjects of animal model experiment.
Figure 3:
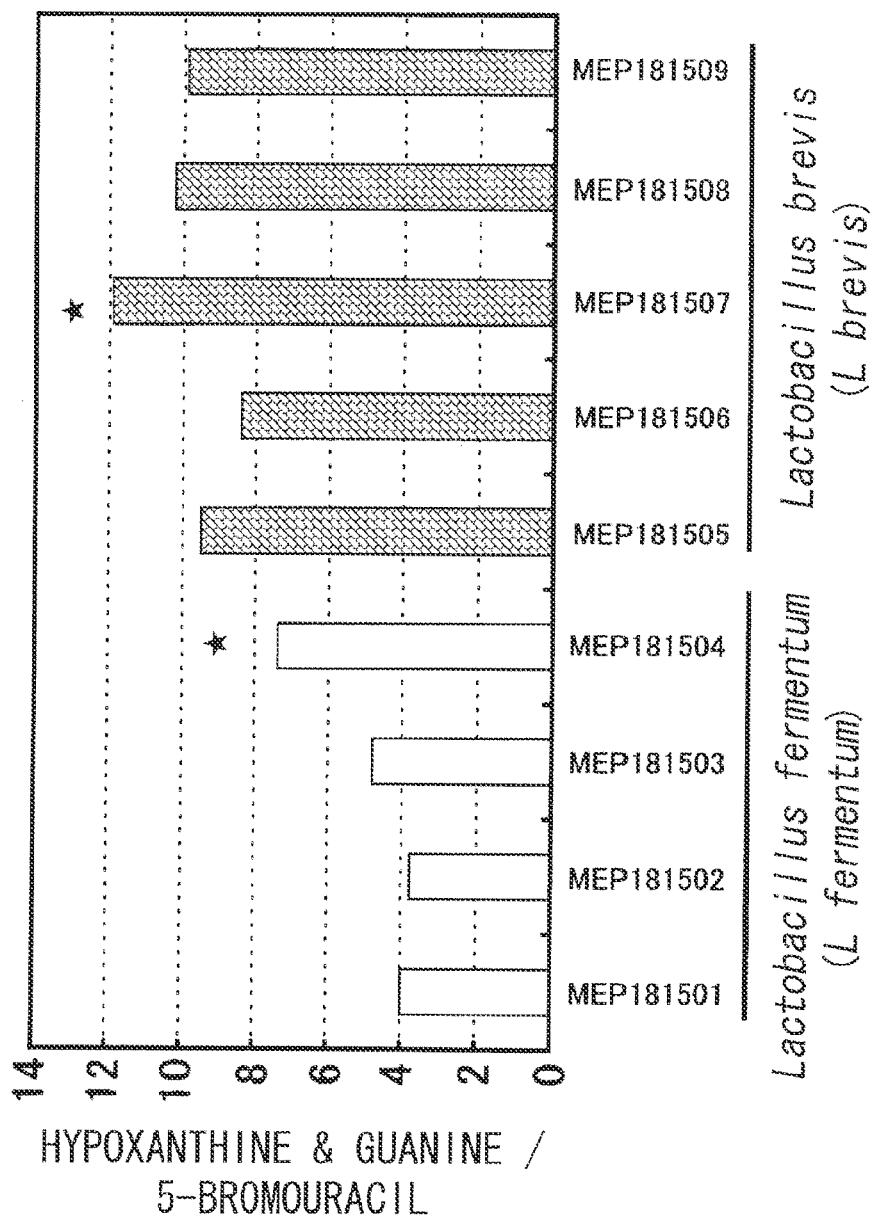
FIG. 3 shows evaluation of the purine-decomposing ability of lactic acid bacteria *L. fermentum* and *L. brevis* by (amount of hypoxanthine+amount of guanine)/amount of 5-bromouracil.

The results are shown in FIGS. 1 to 3. Each compound was quantified based on the peak area values in the HPLC chart. Furthermore, the degradation rates for FIGS. 1 and 2 were calculated according to the following equation:

Degradation rate=100−(amount of inosine or guanosine/amount of inosine or guanosine in the blank)×100.

The calculation method for FIG. 3 is as follows:

(amount of hypoxanthine+amount of guanine)/amount of 5-bromouracil

Based on the results of FIGS. 1 to 3, lactic acid bacteria assessed to have remarkable nucleoside-decomposing ability were selected.

Example 2

In Vivo Experiment Method on the Uric Add-Reducing Effect of Lactic Acid Bacteria Dietary hyperuricemia model animals were produced according to the method described in prior literature (Non-patent Document 1), and the effects of microorganisms (lactic acid bacteria) on the animals' serum uric acid levels were examined. Specifically, the above-mentioned method is a method that prepares a mixed feed containing 2.5 weight % potassium oxonate and 1.0 weight % RNA, feeds rats with the mix, and compares the post-intake blood uric acid levels with those of the negative group and the control group. It has been found that when the model animals in this method are given an oral administration of allopurinol which is an inhibitor of uric acid production, the blood uric acid level in the model animals is significantly suppressed ("Shokuhin kinou kenkyu News (Food Function Research News)" vol. 14, Mar. 9, 2005 issue, Mercian Cleantec Co. environmental inspection center, which can be found on the World Wide Web at m-cleantec.com/gizyutu/news_0503.html). This indicates that the above-mentioned method is useful as a system for evaluating the effectiveness of foods against hyperuricemia.

[2-1 Materials and Experimental Procedure]

[Microorganisms]

Five strains, *Lactobacillus fermentum* strain MEP181504 (hereinafter, "*Lactobacillus*" will be abbreviated as "*L.*" in some cases), *L. brevis* strain MEP181507, *L. gasseri* strain JCM8787, *L. gasseri* strain OLL2959, and *L. oris* strain OLL2779, which were assessed to have high nucleoside-decomposing ability in the above-mentioned in vitro experiment, were used. Bacterial cell suspension solutions were prepared from these various lactic acid bacteria in the same manner as in the in vitro experiments. The bacterial cell suspension solutions were orally administered to rats at $1 \times 10^9$ CFU/10 mL/kg.

[Experimental Animals]

Rats (Wister SPF, male, 7 weeks old) were used. Plastic cages for rats were used for rearing (habituation and testing), and a single rat was housed in each cage. The light-dark cycle was light from 7 a.m. to 7 p.m. (12 hours).

[Preliminary Rearing (Taming) and Group Division]

Experimental animals went through a one-week preliminary rearing (habituation) after they were brought in. During habituation, the animals were allowed to freely consume AIN-93G (Oriental Yeast Co. Ltd.) as feed (food) and tap water as drinking water. After preliminary rearing, blood was collected through the tail vein of rats (seven days after arrival, 8 weeks old, day 0) in a non-fasting state in the morning. This blood was left at room temperature for 30 minutes or more, then serum was fractionated by centrifugal separation at a rotation frequency of 10,000 rpm for 10 minutes, and then the uric acid level in the serum was measured using the phosphotungstic acid method.

Groups were divided such that the serum uric acid level in each group was the same. A total of nine groups with five rats in each group were used in the test: negative groups (Groups 1 and 5), control groups (Groups 2 and 6), and bacterial cell-administered groups (Groups 3, 4, and 7 to 9). The names of the groups, feed, administered substance (administration dose), number of animals, and such are indicated below.

Negative groups (Groups 1 and 5): "AIN-93G" as feed, "physiological saline" was administered (10 mL/kg), five animals.

Control groups (Groups 2 and 6): "AIN-93G admixed with 2.5 weight % potassium oxonate and 1.0 weight % RNA" as feed, "physiological saline" was administered (10 mL/kg), five animals.

Bacterial cell-administered group (Groups 3, 4, and 7 to 9): in each group, "AIN-93G admixed with 2.5 weight % potassium oxonate and 1.0 weight % RNA" as feed, five animals. The administered bacterial cells and doses for each of the groups are as follows:

for Group 3, "a suspension solution of *L. fermentum* strain MEP181504 ($1 \times 10^8$ CFU/mL)" was administered (10 mL/kg), for Group 4, "a suspension solution of *L. brevis* strain MEP181507 ($1 \times 10^8$ CFU/mL)" was administered (10 mL/kg), for Group 7, "a suspension solution of *L. oris* strain OLL2779 ($1 \times 10^8$ CFU/mL)" was administered (10 mL/kg), for Group 8, "a suspension solution of *L. gasseri* strain JCM8787 ($1 \times 10^8$ CFU/mL)" was administered (10 mL/kg), for Group 9, "a suspension solution of *L. gasseri* strain OLL2959 ($1 \times 10^8$ CFU/mL)" was administered (10 mL/kg).

[Main Breeding (Test)]

The test period was set to be eight days from the day after group division, and each of the "AIN-93G" feed (negative groups) and "AIN-93G+potassium oxonate+RNA" feed (control groups and bacterial cell-administered groups) were freely fed to the rats using a diet feeder. The start date of feeding the main feed was set to Day 1, and the subsequent days were counted from this date. The "AIN-93G+potassium oxonate+RNA" feed comprises 2.5 weight % potassium oxonate (100 g, ALDRICH) and 1.0 weight % RNA (500 g, MP Biomedicals Inc.). $1 \times 10^9$ CFU/10 mL/kg of the aforementioned bacterial cell suspension was orally administered by force to the experimental animals of the bacterial cell-administered groups. To the negative groups and control groups, 10 mL/kg of physiological saline solution instead of the bacterial cell suspension was orally administered by force.

[Measurement, Examination, and Such]

Observation of the General Status and Measurement of Body Weight

In all cases (all groups), the general status was observed at the time of administration every day from day 1 to day 8, and the body weight was measured at a fixed time between 9 a.m. and 10 a.m. on days 0, 1, 5, and 8.

Measurement of Feed Consumption and Water Consumption

In all cases (all groups), feed consumption and water consumption were measured at a fixed time between 9 a.m. and 10 a.m. on day 1 (set level), day 5 (residual level, set level), and day 8 (residual level).

Blood Collection and Biochemical Tests

In all cases (all groups), blood was collected from the tail vein on day 0 (in the morning), day 2 (one hour after administration), day 5 (one hour after administration), and day 8 (before administration). The collected blood was subjected to centrifugal separation at a rotation frequency of 10,000 rpm for ten minutes to fractionate the serum, and the uric acid level in the serum was measured by the phosphotungstic acid method. As described above, the serum uric acid levels measured on day 0 were used for group division.

Autopsy and Biochemical Tests

In all cases (all groups), blood collection from the tail vein on day 8 was followed by oral administration of the bacterial cell suspension solution. One hour after administration, whole blood was collected from the abdominal aorta under nembutal (pentobarbital 40 mg/kg) anesthesia and the animal died. The collected blood was centrifuged at a rotation frequency of 3000 rpm for 15 minutes to fractionate the serum, and then creatinine, uric acid, and urea nitrogen in the serum were measured.

Measurement of Organ Weight

The liver was excised from the rat, and its wet weight was measured.

[Statistical Processing]

The results are indicated as the mean±standard deviation, and the control groups were compared with each of the bacterial cell-administered groups. Variance ratios of the numerically converted test values were tested by the F test, Student's t-test was used in the case of equal variance, and Aspin-Welch t-test was used in the case of unequal variance. The statistical analysis of Excel Statistics 2004 was used for statistical processing, and the lowest level of significance was set to 5% on both sides.

[2-2 Results]

Figure 4:
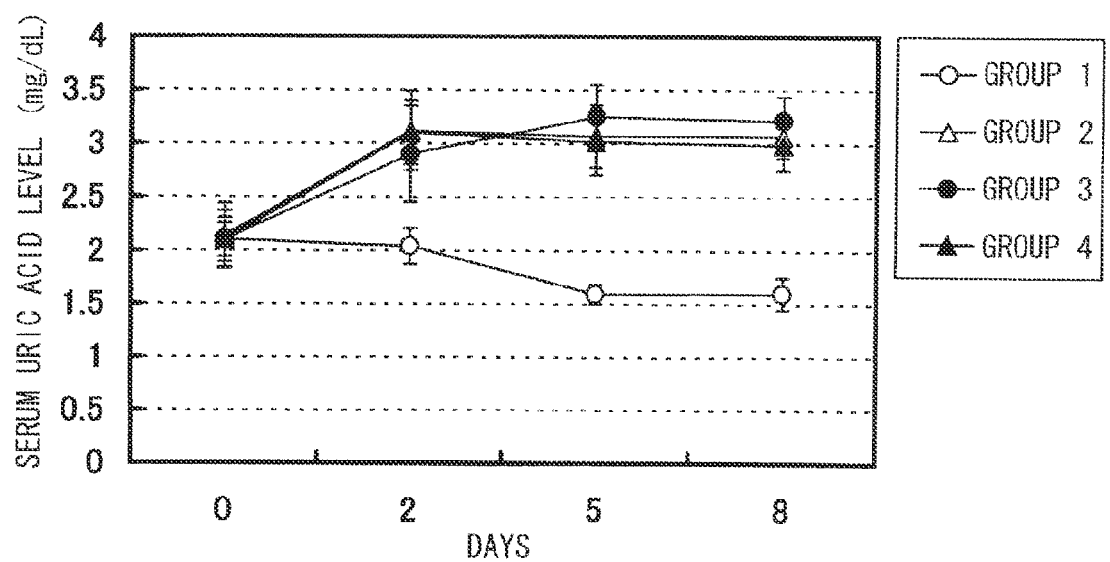
FIG. 4 shows the results of orally administering lactic acid bacteria (*L. fermentum* and *L. brevis*) with high purine-decomposing ability to dietary hyperuricemia model animals, and measuring the serum uric acid level.
Figure 5:
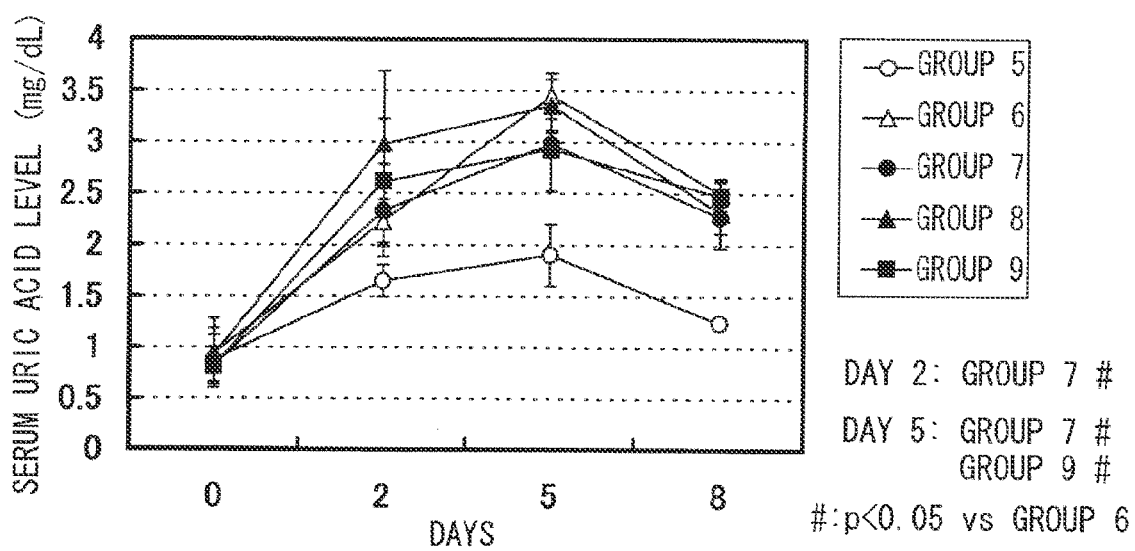
FIG. 5 shows the results of orally administering lactic acid bacteria (*L. oris* and *L. gasseri*) with high purine-decomposing ability to dietary hyperuricemia model animals, and measuring the serum uric acid level. Significant suppression of the increase in serum uric acid levels was observed on day 2 and day 5 after start of administration in the *L. oris* OLL2779 strain-administered group (Group 7), and on day 5 after start of administration in the *L. gasseri* OLL2959 strain-administered group (Group 9) (# in the figure).

The results of the general status are shown in Table 1 (*L. fermentum* and *L. brevis*) and Table 2 (*L. oris* and *L. gasseri*), and the changes in serum uric acid levels are shown in FIGS. 4 and 5.

As shown in FIG. 5, significant difference in the reduction of serum uric acid level as a result of administration of each type of lactic acid bacteria was observed in the *L. oris* OLL2779-administered group and the *L. gasseri* OLL2959-administered group. In terms of general status, there were no problems with the kidney function (creatinine values, serum urea nitrogen, and kidney weight), or body weight, feed consumption, and water consumption in any of the groups. Furthermore, no significant difference in the general status observed was found among the various types of lactic acid bacteria. The scientific characteristics of *L. oris* OLL2779 and *L. gasseri* OLL2959 are shown in Table 3.

TABLE 1

|  | GROUP 1 | GROUP 2 | GROUP 3 | GROUP 4 |
|---|---|---|---|---|
| AMOUNT OF BODY WEIGHT INCREASE DURING THE TESTING PERIOD (g) | 28.6 ± 2.3 | 23.0 ± 2.9 | 20.0 ± 3.5 | 20.0 ± 3.7 |
| FEED CONSUMPTION DURING THE TESTING PERIOD (g) | 106.9 ± 7.7 | 88.2 ± 3.9 | 82.7 ± 4.2 | 85.1 ± 6.3 |
| WATER COMSUMPTION DURING THE TESTING PERIOD (g) | 96.7 ± 15.1 | 192.2 ± 11.9 | 183.3 ± 12.7 | 190.8 ± 16.7 |
| SERUM CREATININE LEVEL (DAY 8) (mg/dL) | 0.7 ± 0.1 | 0.8 ± 0.1 | 0.8 ± 0.1 | 0.8 ± 0.0 |
| AMOUNT OF SERUM UREA NITROGEN (DAY 8) (mg/dL) | 15.5 ± 1.5 | 15.2 ± 2.4 | 16.3 ± 2.0 | 14.8 ± 1.7 |
| ABSOLUTE KIDNEY WEIGHT (DAY 8) (g) | 1.5 ± 0.1 | 1.6 ± 0.0 | 1.6 ± 0.1 | 1.6 ± 0.1 |

TABLE 2

|  | GROUP 5 | GROUP 6 | GROUP 7 | GROUP 8 | GROUP 9 |
|---|---|---|---|---|---|
| AMOUNT OF BODY WEIGHT INCREASE DURING THE TESTING PERIOD (g) | 29.2 ± 2.8 | 18.4 ± 7.3 | 19.2 ± 1.4 | 18.6 ± 4.0 | 21.3 ± 4.5 |
| FEED CONSUMPTION DURING THE TESTING PERIOD (g) | 102.8 ± 7.4 | 87.6 ± 4.7 | 87.8 ± 4.4 | 94.4 ± 12.3 | 87.9 ± 6.7 |
| WATER COMSUMPTION DURING THE TESTING PERIOD (g) | 108.0 ± 13.0 | 170.7 ± 15.3 | 173.0 ± 13.4 | 183.6 ± 8.1 | 168.2 ± 13.1 |
| SERUM CREATININE LEVEL (DAY 8) (mg/dL) | 0.7 ± 0.0 | 0.8 ± 0.1 | 0.7 ± 0.0 | 0.7 ± 0.1 | 0.7 ± 0.0 |
| SERUM UREA NITROGEN LEVEL (DAY 8) (mg/dL) | 14.5 ± 1.1 | 14.5 ± 2.0 | 13.5 ± 0.7 | 15.1 ± 2.4 | 13.1 ± 1.4 |
| ABSOLUTE KIDNEY WEIGHT (DAY 8) (g) | 1.5 ± 0.1 | 1.6 ± 0.0 | 1.6 ± 0.1 | 1.6 ± 0.1 | 1.6 ± 0.1 |

TABLE 3

| | Lactobacillus gasseri OLL2959 (L gasseri OLL2959) (NITE BP-224) | Lactobacillus or is OLL2779 (L or is OLL2779) (NITE BP-223) |
|---|---|---|
| CULTURE CONDITIONS | culture temperature: 37° C. oxygen requirement: facultative anaerobe | culture temperature: 37° C. oxygen requirement: facultative anaerobe |
| COLONY CHARACTERISTICS ON THE MEDIUM (Lactobacilli MRS Agar, DIFCO) | round, pale yellow, smooth type, flat | round, pale yellow, smooth type, flat |
| BACTERIAL FORM | bacillus | bacillus |
| GRAM STAINING | positive | positive |
| FORM OF LACTIC FERMENTATION | homolactic fermentation | homolactic fermentation |
| AEROBIC GROWTH | + | + |
| GROWTH TEMPERATURE | 15° C. − <br> 45° C. + | 15° C. − <br> 45° C. + |
| SUGAR FERMENTABILITY ARABINOSE | − | + |
| XYLOSE | − | + |
| RAMNOSE | − | − |
| RIBOSE | − | + |
| GLUCOSE | + | + |
| MANNOSE | + | − |
| FRUCTOSE | + | + |
| GALACTOSE | + | + |
| SUCROSE | + | + |
| CELLOBIOSE | + | − |
| LACTOSE | − | + |
| TREHALOSE | − | − |
| MELIBIOSE | − | + |
| RAFFINOSE | − | + |
| MELICITOSE | − | − |
| MANNITOL | − | − |
| SORBITOL | − | − |
| GAS PRODUCTION | − | + |

Example 3

Production of Fermented Milk (Example 1 on the Production of Fermented Milk)

Plain yogurt was prepared using *L. gasseri* OLL2959 (NITE BP-224), *L. bulgaricus* JCM1002$^T$, and *S. thermophilus* ATCC 19258. First, bulk starters of *L. gasseri* OLL2959 (NITE BP-224), *L. bulgaricus* JCM1002$^T$, and *S. thermophilus* ATCC19258 were prepared using a 10% powdered skim milk medium. Next a yogurt mix (non-fat milk solid (SNF): 9.5%, fat (FAT): 3.0%) was subjected to heat treatment at 95° C. for five minutes. After heat treatment, this yogurt mix was inoculated with 1% of *L. bulgaricus* JCM1002$^T$ starter, 1% of *S. thermophilus* ATCC19258 starter, and 5% of *L. gasseri* OLL2959 (NITE BP-224) starter, and then fermented at 43° C. for four hours to obtain plain yogurt. This plain yogurt was cooled in the refrigerator (5° C.), and then its flavor and physical properties were checked. Both the flavor and physical properties were satisfactory.

(Example 2 on the Production of Fermented Milk)

Plain yogurt was prepared using *L. oris* OLL2779 (NITE BP-223), *L. bulgaricus* JCM1002$^T$, and *S. thermophilus* ATCC19258. First, bulk starters of *L. oris* OLL2779 (NITE BP-223), *L. bulgaricus* JCM1002$^T$, and *S. thermophilus* ATCC19258 were prepared using a 10% powdered skim milk medium. Next a yogurt mix (non-fat milk solid (SNF): 9.5%, fat (FAT): 3.0%) was subjected to heat treatment at 95° C. for five minutes. After heat treatment, this yogurt mix was inoculated with 1% of *L. bulgaricus* JCM1002$^T$ starter, 1% of *S. thermophilus* ATCC19258 starter, and 5% of *L. oris* OLL2779 (NITE BP-223) starter, and then fermented at 43° C. for four hours to obtain plain yogurt. This plain yogurt was cooled in the refrigerator (5° C.), and then its flavor and physical properties were checked. Both the flavor and physical properties were satisfactory, and this confirmed that *L. oris* OLL2779 can be used favorably for manufacturing food.

INDUSTRIAL APPLICABILITY

The present invention provides lactic acid bacteria capable of reducing the blood uric acid level. Since oral intake of the lactic acid bacteria of the present invention can lower blood uric acid levels, the lactic acid bacteria of the present invention can be used as foods or pharmaceuticals for preventing and/or treating gout or hyperuricemia. In particular, it has been confirmed that the problem of gas production does not happen when the lactic acid bacteria of the present invention are used in food manufacturing, and thus they are likely to be suitable for practical applications. Furthermore, it may become possible to manufacture processed foods with reduced purine levels by using the lactic acid bacteria of the present invention. This way, the lactic acid bacteria of the present invention are likely to be very highly useful for the food and pharmaceutical industry.

The invention claimed is:

1. A lactic acid bacterium *Lactobacillus gasseri* strain OLL2959 deposited as Accession No.: NITE BP-224, wherein the lactic acid bacterium is a biologically pure culture thereof.

2. A dietary product for suppressing an increase in blood uric acid level, comprising the lactic acid bacterium of claim 1, and/or a substance containing said lactic acid bacterium.

3. A pharmaceutical for suppressing an increase in blood uric acid level, comprising the lactic acid bacterium of claim 1, and/or a substance containing said lactic acid bacterium.

4. A pharmaceutical for treating hyperuricemia, comprising the lactic acid bacterium of claim 1, and/or a substance containing said lactic acid bacterium.

5. A dietary product for treating hyperuricemia, comprising the lactic acid bacterium of claim 1, and/or a substance containing said lactic acid bacterium.

6. A method for suppressing the level of purine ingested from food, wherein the method comprises administering the lactic acid bacterium of claim 1, and/or a substance containing said lactic acid bacterium.

7. A method for suppressing an increase in blood uric acid level, wherein the method comprises administering the lactic acid bacterium of claim 1, and/or a substance containing said lactic acid bacterium.

8. A method for producing a dietary product with reduced purine level, wherein the method comprises the step of contacting a raw material or intermediate product of the dietary product with the lactic acid bacterium of claim 1, and/or a substance containing said lactic acid bacterium.

9. A method for treating any one or more diseases or symptoms from the group consisting of hyperuricemia, gout, renal dysfunction, urinary stone, and arteriosclerosis, wherein the method comprises administering the lactic acid bacterium of claim 1, and/or a substance containing said lactic acid bacterium.

* * * * *

UNITED STATES PATENT AND TRADEMARK OFFICE
CERTIFICATE OF CORRECTION

| | |
|---|---|
| PATENT NO. | : 8,460,918 B2 |
| APPLICATION NO. | : 12/745007 |
| DATED | : June 11, 2013 |
| INVENTOR(S) | : Hiroshi Tsuboi |

It is certified that error appears in the above-identified patent and that said Letters Patent is hereby corrected as shown below:

On the Title Page, change Item (73) Assignee: Meiji Co., Ltd., Kanagawa (JP) – TO –

(73) Assignee: Meiji Co., Ltd., Tokyo (JP)

Signed and Sealed this
Eighth Day of April, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,460,918 B2  Page 1 of 1
APPLICATION NO. : 12/745007
DATED : June 11, 2013
INVENTOR(S) : Tsuboi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 222 days.

Signed and Sealed this
Eighth Day of September, 2015

Michelle K. Lee
*Director of the United States Patent and Trademark Office*